United States Patent [19]

Wason et al.

[11] Patent Number: 5,225,177

[45] Date of Patent: Jul. 6, 1993

[54] DENTIFRICE ABRASIVES AND COMPOSITIONS

[75] Inventors: Satish K. Wason, Bel Air; William C. Fultz, Rising Sun, both of Md.

[73] Assignee: J.M. Huber Corporation, Rumson, N.J.

[21] Appl. No.: 467,423

[22] Filed: Jan. 19, 1990

[51] Int. Cl.$^5$ .............................................. C01B 33/32
[52] U.S. Cl. ...................................... 423/339; 423/335; 51/308; 424/49
[58] Field of Search ................... 51/308, 298; 423/324, 423/325, 335, 339

[56] References Cited

U.S. PATENT DOCUMENTS

| | | | |
|---|---|---|---|
| 2,649,388 | 8/1948 | Wills et al. | 51/308 |
| 2,744,001 | 5/1056 | Harman et al. | 51/308 |
| 4,110,083 | 8/1978 | Benedict | 51/298 |
| 4,122,160 | 10/1978 | Wason | 51/308 |
| 4,122,161 | 10/1978 | Wason | 51/308 |
| 4,144,321 | 3/1979 | Wason | 106/492 |
| 4,244,707 | 1/1981 | Wason | 51/308 |
| 4,280,822 | 7/1981 | Wason | 51/308 |
| 4,340,583 | 7/1982 | Wason | 51/308 |
| 4,463,108 | 7/1984 | Wagner et al. | 106/492 |
| 4,857,289 | 8/1989 | Nauroth et al. | 423/335 |
| 4,874,594 | 10/1989 | Chevallier | 42/335 |
| 4,992,251 | 2/1991 | Aldcroft et al. | 423/335 |

Primary Examiner—Mark L. Bell
Assistant Examiner—Margaret Einsmann
Attorney, Agent, or Firm—Harold H. Flanders; Robert L. Price; Alec H. Horn

[57] ABSTRACT

Novel precipitated silicon dioxide abrasive compositions which can be incorporated into therapeutic toothpaste compositions containing soluble fluoride salts are disclosed. The abrasives comprise low structure, high fluoride compatible amorphous precipitated silicon dioxides (silicas) having a controlled refractive index for use in low water clear gel dentifrice applications. Also provided are methods for preparation of the novel silicon dioxide abrasives and resulting toothpaste formulations containing such abrasives.

2 Claims, No Drawings

DENTIFRICE ABRASIVES AND COMPOSITIONS

BACKGROUND OF THE INVENTION

1. Field of the Invention

This invention relates to improved dentifrice abrasives. More particularly, the present invention relates to novel, high fluoride compatible amorphous precipitated silica abrasives which are suitable for use in therapeutic toothpaste compositions containing soluble fluoride salts. The invention further relates to methods for preparing these improved precipitated silica abrasives and to toothpastes containing the improved abrasives including toothpaste embodiments. Such toothpaste compositions exhibit both high fluoride compatibility and high cleaning performance.

2. The Prior Art

The function of an abrasive substance in formulations intended for use in the oral cavity is to remove various deposits, including pellicle film, from the surface of the teeth. Pellicle film is tightly adherent and often contains brown or yellow pigments and thus imparts an unsightly appearance to the teeth. An advantageous toothpaste abrasive material should maximize film removal without causing undue abrasion to the hard tooth tissue. Dental researchers are continually concerned with developing toothpaste abrasives which demonstrate satisfactory levels of cleaning and which are not unduly abrasive and damaging to the oral tissue.

In addition to abrasives, therapeutic toothpastes typically contain fluoride ion sources. The beneficial reduction in the incidence of dental caries resulting from the topical application to dental enamel surfaces of solutions containing fluoride ions is well known. Especially at solution pH's between about 4 and 8, fluoride ions are believed to interact with enamel to reduce the acid solubility of such enamel. Enamel so treated with fluoride is more resistant to the formation of dental caries. Accordingly, therapeutic toothpaste compositions are formulated to provide fluoride ion availability in brushing solutions formed in the oral cavity during use.

It has been postulated that the effectiveness of fluoride treatment in providing enamel antisolubility/anticariogenic benefits is dependent upon the amount of fluoride ion which is available for uptake by the enamel being treated. It is, of course, therefore desirable to formulate toothpaste compositions which provide maximum fluoride ion availability in brushing solutions formed therefrom. However, efforts to utilize such ionic fluoride anticariogenic agents in toothpastes suitable for home use have been unable to provide the theoretical maximum soluble fluoride because of the tendency for ionic fluoride to be inactivated and thereby rendered unavailable for enamel uptake. That is, the toothpastes lose, upon storage (at rates which increase with temperature), the capability of providing the theoretical maximum amount of soluble fluoride. For purposes of this invention, the "soluble fluoride" content of any given toothpaste composition refers to the ppm concentration of fluoride ion which is found in the supernatant sample centrifuged from 1:3 by weight slurry of the toothpaste in water (1:3=toothpaste:water).

Fluoride ion sources tend to interact with toothpaste impurities and with such toothpaste components as abrasives, buffers, etc. Such interaction diminishes the ability of the fluoride source to provide "soluble fluoride" upon use. The propensity of the toothpaste compositions herein to maintain their levels of soluble fluoride after storage is expressed hereinafter as "toothpaste fluoride compatibility". Thus, the toothpaste fluoride compatibility of a particular toothpaste composition is that percentage of the theoretical maximum amount of fluoride source that is actually measured as soluble fluoride after storage for a specified time and at a specified temperature (e.g. one week at 120° F.). Similarly, the propensity of such a dentifrice component such as the abrasive to interact with the fluoride source to diminish the measured "soluble fluoride" level from the theoretical maximum amount of fluoride source (particularly in the presence of pellicle film penetration agents) is expressed as "abrasive fluoride compatibility". The test procedures used herein to determine "toothpaste fluoride compatibility" values and "abrasive fluoride compatibility" values are described more fully hereinafter.

One toothpaste component which can pose special difficulties in formulating fluoride toothpastes is a precipitated silica abrasive component. Precipitated silica abrasives are desirable for use in toothpastes since they have desirably low dentin abrasion values. Certain prior art precipitated silica abrasives are generally compatible with soluble fluoride sources but have insufficiently high abrasivity to provide effective cleaning performance. Certain other prior art precipitated silica abrasives provide acceptable cleaning performance but have low abrasive fluoride compatibility as measured by the method hereinafter. There is a clean need to formulate precipitated silica abrasives which exhibit high "abrasive fluoride compatibility" as well as acceptable cleaning performance. Accordingly, it is an object of the present invention to provide precipitated silica abrasives which exhibit high "abrasive fluoride compatibility" as well as acceptable cleaning performance.

It is of course well known that therapeutic toothpaste compositions contain calcium phosphate materials as abrasives. These calcium materials are present in large amounts as described above and illustrated for example in U.S. Pat. No. 3,624,199, issued Nov. 30, 1971, Norfleet et al, and U.S. Pat. No. 3,864,471, issued Feb. 4, 1975, Mills et al. Toothpaste compositions are also known in the art which contain small amounts of alkaline earth metal ions, such as calcium ions, and compositions of this type are illustrated by U.S. Pat. No. 3,991,177, issued Nov. 9, 1976, Vidra et al. This patent discloses toothpaste compositions which contain a stabilizer-activator for a dextranase enzyme agent with the stabilizer-activator being a salt such as calcium chloride present in an amount of 0.001 to 0.3 weight percent. This composition can also contain therapeutic fluoride and the abrasive agent is calcium carbonate.

Other prior art which discloses toothpaste compositions containing alkaline earth metal compounds or ions include U.S. Pat. No. 3,095,356, issued Jun. 25, 1963, to Moss; U.S. Pat. No. 3,122,483, issued Feb. 25, 1964, to Rosenthal; U.S. Pat. No. 3,669,221, issued Jun. 13, 1972, to Hase; U.S. Pat. No. 3,782,446, issued Jan. 1, 1974, to Walter; U.S. Pat. No. 3,842,168, issued Oct. 15, 1974, to Colodney; and, U.S. Pat. No. 3,689,537, issued Sep. 5, 1972, to Kuder.

SUMMARY OF THE INVENTION

There is provided by the present invention a novel abrasive material for toothpaste compositions which comprises in its broadest embodiment, the manufacture of abrasive precipitated silicas with oil absorptions less than 125 cc/100 g having excellent abrasive properties and able to provide superior viscosity build in low water formulations. Low water formulations in general have less then 10% added water. These silicas are prepared using sodium silicate and acid by carefully controlling the batch making parameters. The present invention is thus particularly useful in low water clean gel formulations having high fluoride (especially sodium fluoride) availability with time. Also provided is a method for the preparation of the novel abrasives of this invention.

The present invention further relates to fluoride-containing toothpaste compositions which exhibit minimal loss of soluble fluoride upon storage at normal temperatures and which provide excellent cleaning performance. Such toothpaste compositions comprise the amorphous, precipitated silica abrasives of the present invention, a source of fluoride ions, a binding agent, a humectant and water.

The amorphous, precipitated silica abrasives of the present invention comprise from about 6% to 35% by weight of the toothpaste compositions.

The fluoride ion source comprises from about 0.01% to 3.0% by weight of the toothpaste compositions and can be any water-soluble material which yields fluoride ions in aqueous solution.

The binder comprises from about 0.2% to 2% of the toothpaste compositions.

The humectant comprises from about 5% to 55% by weight of the toothpaste composition. The water in the toothpastes herein comprises less than 10% by weight of the composition.

DETAILED DESCRIPTION OF THE INVENTION

The present invention relates to novel, precipitated silicon dioxide dentifrice abrasives, methods for their preparation, and their incorporation into toothpastes to provide resulting compositions having excellent toothpaste fluoride compatibility values and excellent abrasivity values. The toothpaste compositions herein further essentially comprise a water-soluble fluoride ion source, a binding agent, and certain amounts of humectants and water. Each of these components as well as optional ingredients, composition use and composition preparation are described in detail as follows:

The present invention relates to the manufacture of abrasives precipitated silicas having oil absorptions less than 125 cc/100 g, excellent abrasive properties and which are able to provide superior viscosity build in low water formulations, where low water formulations as the term is used herein are those having less than 10% added water. These silicas are prepared using sodium silicate and acid by carefully controlling the batch making parameters.

The present invention is particularly useful in low water clear gel formulations which are desired to have high fluoride availability with time especially when the source of fluoride is sodium fluoride.

The manufacture of clear gel dentifrices using silica requires the careful matching of the refractive index of the humectant system to that of the silica. In the prior art there have been attempts to achieve this end by changing the index of refraction of the silica to match the system by the addition of $Al^{+++}$ ions during the manufacture of the silica. In some instances, the addition of $Al^{+++}$ ions may result in a lack of compatibility of the silica with sodium fluoride.

In general, there is in the prior art no known method to control the refractive index of a silica without an additive at a given structure level or oil absorption.

Prior art amorphous precipitated silicas, in general, require high water loadings, in excess of 10% added water, due to their low refractive indexes. The only silica products which are presently known to work in low water formulations are silica gels due to their inherently higher refractive indexes. These silica gels, however, are not able to be used in clear gel dentifrice formulations at a greater than 6% water loadings and are generally poor in viscosity build.

The products of the present invention make clear gel dentifrices at 4 to 10% water loadings while providing excellent cosmetic and therapeutic dentifrice properties.

EXAMPLE 1

623 gallons of fresh water is added to a suitably-sized reactor to function as the starting reaction medium. The water is heated to 205±2° F. A 13.3% concentration of 2.65 M.R. silicate at 183° F. is added for 0.75 minutes. At the end of the 0.75 minutes silicate addition and 11.4% concentration of sulfuric acid is initiated and continued for 60.75 minutes. The acid is added at the rate of 36.5 gpm. The silicate is added at the rate of 71.3 gpm. At 60.75 minutes, both the acid and the silicate are terminated. The batch is treated with acid to pH of 5.2. The batch is then digested for 10 minutes at 205° F. and the pH adjusted to 5.3.

The resulting product has a moisture of 10%, a 5% pH of 7.0, an oil absorption of 100 cc/100 g, a refractive index of 1.45, an APS of 11 microns and a density of 17 lbs/cu.ft.

EXAMPLE 2

The procedure of EXAMPLE 1 was repeated with a reaction temperature of 195° F. and a digestion temperature of 200° F. to produce substantially the same product.

EXAMPLE 3

The procedure of EXAMPLE 2 was repeated using 3.3 M.R. silicate, a reaction temperature of 190° F. and a digestion temperature of 216° F. The resulting product was substantially as described above with an oil absorption of 115 cc/100 g. .

The viscosity of the above-described products was 325 Kcps with 10% haze, RDA of 80.

A clear gel therapeutic toothpaste with 6% $H_2O$ was produced using the product of EXAMPLE 1 at 18% within 64.3% Sorbital, 0.5% CMC-MF, 0.24% sodium fluoride, 0.5% sodium benzoate, 0.1% sodium saccharin, 3% carbowax, and 5% silica thickener with 0.3% color blue #1, 1% SL.S., and 1% flavor.

PRECIPITATED SILICA DENTAL ABRASIVE

The present invention relates to low structure precipitated silicon dioxide materials which are suitable for use as dental abrasives. Such abrasives have been described above. This dental abrasive material is characterized further by having a percent abrasive fluoride compatibility in the range of at least 90%, a RDA of at least 40, preferably from about 70 to 120, a loss on ignition (hereinafter "LOI") in the range of 9-17%, a density in the range of about 15-18.5 $\#/ft.^3$, an oil absorption in the range of about 85-115 cc/100 grams and a BET surface area in the range of about 50-250 $m^2/g$ with an average particle size in the range of 8-14 microns. When incorporated into a toothpaste, the dental abrasives herein provide high fluoride compatibility and excellent cleaning performance.

TOOTHPASTES

Also provided by the present invention herein are therapeutic toothpastes containing the instant novel precipitated silica abrasives. In addition to the instant abrasives, the toothpaste compositions of the present invention further comprise certain amounts of a water-soluble fluoride ion source, a binding agent, a humectant and water. Each of these additional toothpaste components as well as optional toothpaste components are described in detail as follows:

A. Abrasive

As indicated above, the instant precipitated silica abrasives are particularly suitable for incorporation into fluoride-containing therapeutic toothpaste compositions. Therapeutic toothpastes employing such abrasives provide satisfactory tooth cleaning performance and also possess excellent abrasive fluoride compatibility characteristics. The instant toothpaste compositions essentially contain from about 6% to 35%, preferably from about 10% to 20%, by weight of the instant precipitated silica abrasives.

B. Fluoride Ion Source

The instant therapeutic toothpaste compositions further contain from about 0.01% to 3%, preferably from about 0.1% to 1.0%, by weight of a water-soluble, fluorine-containing material which yields fluoride ions in aqueous solutions. Such fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970, and Widder et al; U.S. Pat. No. 3,678,154; issued Jul. 18, 1972, both patents being incorporated herein by reference. Preferred fluoride ion sources for use herein include sodium fluoride (NaF), stannous fluoride ($SnF_2$), potassium fluoride (KF), potassium stannous fluoride ($SnF_2$-KF), indium fluoride ($InF_3$), zinc fluoride ($ZnF_2$), ammonium fluoride ($NH_4F$), and stannous chlorofluoride (SnClF). Sodium fluoride and stannous fluoride are particularly preferred as well as mixtures thereof.

Preferably, the instant toothpaste compositions provide from about 50 ppm to 500 ppm, more preferably from about 100 to 400 ppm, of fluoride ions in the aqueous solutions which contact dental surfaces when the toothpastes of the present invention are used in the mouth. As described more fully hereinafter, such solutions are simulated by preparing 3:1 water/toothpaste slurries (by weight) of the toothpaste compositions herein and by subsequently centrifuging such slurries to obtain an aqueous supernatant. The fluoride ion concentration in such a supernatant is taken as a measure of the "soluble fluoride" provided by any given fluoride toothpaste composition.

C. Binder

A binder is essentially employed to prevent separation of the liquid and solid phases in the toothpaste compositions herein. Such binder materials are well known in the toothpaste art. The most conventionally used binders are the seaweed colloids such as Carrageenen (Irish moss or Viscarin ®) and derivatives of cellulose, such as sodium carboxymethyl cellulose and hydroxyethyl cellulose. Another type of binder which is suitable for use herein is gums such as 1) vegetable gums, e.g., guar gums and 2) fermentation products, e.g., xanthan gum. The binder component generally comprises from about 0.1% to 5%, preferably 0.2% to 2% by weight of the toothpaste compositions herein. Since the natural and synthetic water dispersions of water binders are subject to microbial or mold attack, the toothpastes herein can optionally contain a relatively small amount of a preservative. Examples of preservatives typically employed are the esters of parahydroxyl benzoates.

Toothpaste binders are more fully described in Hager et al, U.S. Pat. No. 2,839,448, issued Jun. 17, 1958; and DiGiulio, U.S. Pat. No. 3,962,307, issued Jan. 21, 1975. These patents are incorporated herein by reference.

D. Humectant

Another essential component of the toothpaste compositions herein is a humectant. Suitable humectant materials are also well known in the toothpaste art. The humectant serves to retain moisture and thereby to keep the toothpaste compositions from hardening upon exposure to air. Certain humectants can also impart desirable sweetness or flavor to toothpaste compositions. The humectant generally comprises from about 5% to 55%, preferably from about 20% to 36%, by weight of the toothpaste compositions herein.

Suitable humectants for use in this invention include edible polyhydric alcohols such as glycerine, sorbitol, xylitol and propylene glycol. Sorbitol is frequently employed as a 70% aqueous solution known as Sorbo ®. Mixtures of glycerine and sorbitol are especially preferred as the humectant component of the toothpaste compositions herein.

E. Water

Water is another essential element of the toothpastes of this invention. Water employed in the preparation of commercially-suitable toothpastes should be deionized and free of organic impurities. Water comprises less than 10% added water.

F. Optional Ingredients

In addition to the above described essential components, the toothpastes of this invention can contain a variety of optional conventional toothpaste ingredients. Such optional ingredients include (1) sudsing agents, (2) pellicle film penetration agents, (3) flavoring and sweetening agents, (4) anticalculus, antiplaque agents, and (5) pigments and coloring agents.

1) Sudsing Agent

A preferred optional ingredient is a sudsing agent. Suitable sudsing agents are those which are reasonably stable and form suds throughout a wide pH range, i.e., non-soap anionic, nonionic, cationic, zwitterionic and amphoteric organic synthetic detergents. Sudsing agents of these types are described more fully in Agricola et al; U.S. Pat. No. 3,959,458; issued May 25, 1976, and in Haefele; U.S. Pat. No. 3,937,807; issued Feb. 10, 1976. Both of these patents are incorporated herein by reference.

Anionic sudsing agents useful herein include the water-soluble salts of alkyl sulfates having from 8 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the toothpastes of the present invention can be broadly defined as compounds produced by the condensation of alkylene oxide groups (hydrophilic in nature) with an organic hydrophobic compound which may be aliphatic or alkyl-aromatic in nature. Examples of suitable nonionic sudsing agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing agents useful in the toothpastes of the present invention can be broadly described as derivatives of aliphatic quaternary ammonium phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate.

The cationic sudsing agents useful in the toothpastes of the present invention can be broadly defined as quaternary ammonium compounds having one long alkyl chain containing from about 8 to 18 carbon atoms such as lauryl trimethylammonium chloride; cetyl pyridinium chloride; cetyl trimethylammonium bromide; di-isobutyl-phenoxyethoxyethyl-dimethyobenzylammonium chloride; coconutalkyltrimethylammonium nitrite; cetyl pyridinium fluoride, etc. Especially preferred are the quaternary ammonium fluorides described in U.S. Pat. No. 3,535,421, Briner et al, issued Oct. 20, 1970, incorporated by reference hereinbefore, where said quaternary ammonium fluorides have detergent properties. The cationic sudsing agents can also act as germicides in certain of the toothpastes herein.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to 18 carbon atoms and one contains an anionic water-solubilizing group, e.g., carboxylate, sulfonate, sulfate, phosphate or phosphonate.

The sudsing agent can be present in the toothpaste compositions of this invention in an amount from 0.1% to 6% by weight of the total composition.

If present, such pellicle penetration agents comprise from about 0.2 to 5.0% by weight of the toothpaste composition.

2) Flavoring Agents

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, acetosulpham, dihydrochalcones and sodium cyclamate. Flavoring agents are generally used in toothpastes at levels of from about 0.01% to 2% by weight and sweetening agents at levels of from about 0.05% to about 3% by weight.

3) Antiplaque/Anticalculus Agent

Phosphorus-containing anticalculus agents and/or bis-biguanide antiplaque agents can also optionally be added to the toothpastes of this invention. Phosphorus-containing anticalculus agents such as disodium ethane-1-hydroxy-1, 1-diphosphonate and related materials are described more fully in McCune et al; U.S. Pat. No. 3,488,419, issued Jan. 6, 1970, incorporated herein by reference. Bis-Biguanide antiplaque agents such as chlorhexidine (1,6-bis[$N^5$-p-chlorophenyl-$M^1$-biguanido]hexane), the soluble and insoluble salts thereof and related materials such as 1,2-bis($N^5$-p-trifluoromethylphenyl-$N^1$-biguanido) ethane are described more fully in Haefele, U.S. Pat. No. 3,934,002, issued Jan. 20, 1976; Haefele, U.S. Pat. No. 3,937,807, issued Feb. 10, 1976; Procter & Gamble, Belgian Patent 843,244, published Dec. 22, 1976, and Procter & Gamble, Belgian Patent 844,764, published Jan. 31, 1977. These patents are incorporated herein by reference.

If present, the optional anticalculus and/or antiplaque agents generally comprise from about 0.01% to 2.5% by weight of the toothpaste compositions herein.

4) Pigments and Coloring Agents, Misc

A variety of other optional components well known in the art may be added to the toothpaste compositions herein to improve the usual aesthetics. These include pigments, dyes, speckles and the like. When present, these optional components generally comprise from about 0.001 to about 2% by weight of the toothpastes herein.

COMPOSITION PREPARATION

Toothpaste compositions of the present invention are prepared simply by mixing together in any order and by any conventional means the essential and optional components herein. Once prepared, the compositions herein provide a pH of from about 4.0 to 8.0, preferably 6.5 to 7.5, when said compositions are slurried with water in a 3:1 weight ratio of water to composition. Fluoride toothpastes providing pH values within the 4.0 to 8.0 range provide especially effective dental enamel antisolubility benefits compared to toothpastes with pH values outside this range. Flavoring of toothpastes within this pH range is also comparatively easy.

COMPOSITION USE

Toothpaste compositions of the present invention are used in conventional manner. The toothpaste compositions or slurries thereof are brushed onto dental surfaces and subsequently rinsed away.

During use of the toothpaste herein in conventional manner, pastes or slurries generally contact dental surfaces for at least about 30 seconds. More preferably such pastes or slurries contact dental surfaces for at least about 60 seconds.

TESTING AND EVALUATION

The precipitated silica abrasives herein can be used to prepare especially desirable therapeutic toothpaste compositions containing soluble phosphate pellicle film penetration agents. Such compositions provide both high abrasive fluoride compatibility and yet have good tooth cleaning performance. The following tests and evaluation serves to demonstrate the excellent fluoride compatibility provided by the precipitated silica dental abrasives herein in the toothpaste composition of the present invention.

Abrasive Fluoride Compatibility

Precipitated silica dental abrasives can be screened for their relative compatibility with fluoride materials by means of a 24-hour abrasive slurry test. Such a test can be used to generate date which can predict the availability of soluble fluoride in certain types of fluoride toothpastes after storage over approximately a four-week period at 80° F.

The 24-hour abrasive slurry test is used to generate fluoride compatibility values which are defined as that percentage of theoretical maximum available fluoride by the following test method. In this method (Orion Specific Ion Electrode Method) a standard sodium fluoride stock solution containing 1624 ppm of fluoride is prepared by dissolving 2.80 grams of sodium fluoride, 21.5 grams of $NaH_2PO_4$ and 83.4 grams of $Na_2HPO_4 \cdot 2-H_2O$ in 672.5 gram of deionized distilled water and stored in a polyethylene bottle. Thirty (30) grams of this solution is then weighed out. Seven (7) grams of the silica abrasive being tested is then dispersed into the solution and contacted for 24 hours at a temperature of about 100° F. (37.8° C.). After 24 hours, the precipitated silica abrasive/fluoride solution is centrifuged for 20 minutes at 15,000 rpm or until the supernatant is clear. Then 10 ml. of the supernatant is pipetted into a plastic vial. Thereafter, 10 ml. of EDTA/THAM solution is likewise pipetted into the plastic vial. (The EDTA/THAM solution is a 0.2 molar in EDTA (ethylene diaminetetraacetic acid, disodium salt) and 0.2 molar in THAM (2-Amino-2-hydroxymethyl-1,2-propanediol) and adjusted to pH 8.0 with sodium hydroxide.) a magnetic stirring bar is added and gently stirring is initiated. The fluoride ion concentration is determined by direct potentiometry with the Orion fluoride electrode (Model 95-09). Emf is converted to parts per million (ppm) fluoride in the supernatant by means of a logarithmic equation. The fluoride compatibility value is then calculated by expressing the measured ppm soluble fluoride as a percentage of the theoretically available soluble fluoride.

Abrasive Fluoride Compatibility in Toothpastes

Preferred toothpastes herein containing precipitated silica abrasives and pellicle film penetration agents are evaluated for abrasive fluoride compatibility. The toothpastes which are prepared for evaluation have the composition of the toothpaste of Example 8 and differ only in the variation of the abrasive component.

To determine fluoride compatibility values for the toothpastes tested, a soluble fluoride determination method is used which is similar to the method described above for the determination of abrasive fluoride compatibility values. In this method, the toothpaste compositions are stored for a specified length of time in a laminate tube. Thereafter, 15.0 grams of the composition is placed in a 100 ml. beaker and then 45.0 grams of distilled water is added. The mixture then is stirred to form a slurry in which the toothpaste is uniformly dispersed. The slurry is subsequently centrifuged for 20 minutes at 15,000 rpm or until the supernatant is clear.

The supernatant is then treated as in the abrasive fluoride compatibility determination method described above. Soluble fluoride concentration is similarly measured and an abrasive fluoride compatibility value for each toothpaste is similarly calculated.

Cleaning Performance

The dental cleaning ability of the silica abrasives herein can be estimated by means of Radioactive Dentin Abrasion (RDA) testing. RDA values can be used to estimate the relative cleaning performance of various abrasives for any given type of dentifrice abrasive. Thus, for precipitated silica abrasives, an RDA value (measured by the method provided below) of at least 40, preferably between 70 and 120, is needed to insure that the abrasive has sufficient abrasivity to be an effective dentifrice cleaner.

The method which is employed for determining the RDA values for toothpastes is described in the *Journal of Dental Research*, July–August 1976, by Hefferren, pp. 563–573. The specific steps for determining RDA values are set forth as follows:

A. Selection and Preparation of Teeth

Sound, single-rooted permanent teeth that are caries-free and vital at extraction are selected. Teeth are then scraped clean with a scalpel. The crown and root tip of each tooth are removed using an abrasive disc so as to prepare a dentin sample 14 mm long and at least 2 mm wide at the narrower end. Cut pieces of root (dentin chips) or, alternatively, an additional tooth, are also prepared to be later used in determining a correction factor for self-absorption of radiation.

B. Irradiation of Dentin

The prepared roots and dentin chips described in Step A are exposed to a neutron flux of $2 \times 10^{12}$ neutrons/cm$^2$ for three hours.

Mounting of Roots

After irradiation, the irradiated roots are embedded in a mount of cold-curing dental methacrylate resin and mounted onto a cross-brushing machine. Toothbrushes used throughout the test are 50-Tuft, medium, flat, "Pepsodent" toothbrushes.

D. Preconditioning the Dentin Surfaces

Prior to to initial test run, the freshly mounted, irradiated roots are brushed with a reference slurry (10g calcium pyrophosphate +50 ml. of a 0.5% CMC-10% glycerine solution) for 6,000 brush strokes. At the beginning of each subsequent day's test run, the roots are brushed for 1,000 strokes.

E. Test Run

After preconditioning, the dentin samples are then conditioned with the reference slurry (same slurry as in Step D) for 1,500 brush strokes at the beginning, during and end of each test run. The test run consists of brushing dentin samples for 1,500 brush strokes with a slurry of test product (25g dentifrice+40 ml. deionized of distilled water).

F. Preparation of Correction Factors

The correction factors are prepared by dissolving the dentin chips or, alternatively, an additional tooth, from Step B in 5 ml. conc. HCl brought to a volume of 250 ml. with distilled water. One ml. of this solution is added to test pastes and reference slurries which are prepared similarly to those in Step E, and then neutralized with 0.1 N NaOH.

Radioactive Tracer Counting

The radioactivity of the slurry samples (1.0 ml.) is determined with an Intertechnique SL-30 liquid scintillation counter. Alternate counting procedure: 3 ml. aliquots of each slurry are transferred to stainless steel; flat-bottom 1-inch×5/16-inch planchets and counted using Nuclear Chicago Geiger Counting System.

Calculations

The radioactive dentin abrasion value (RDA) for a particular paste will be the ratio of the average corrected counts for that paste to the average count for the reference multiplied by 100. The reference abrasive is given an arbitrary dentin abrasion value of 100 units.

We claim:

1. A low structure amorphous silicon dioxide prepared b adding a 13.3% solution of 2.65 Molar Ratio sodium silicate at 183° F. for 0.75 minutes to fresh water, continuing said addition of sodium silicate and adding 11.4% sulfuric acid for 60.75 minutes, said acid being added at the rate of 36.5 gpm and said sodium silicate being added at the rate of 71.3 gpm; adjusting the pH to 5.2 and digesting for 10 minutes at 205° F. and thereafter adjusting the pH to 5.3 to produce a product having 10% moisture, 5% pH of 7.0, oil absorption of 100 cc/100 gm, a refractive index of 1.45, an APS of 11 microns, a density of 17 lbs/cu. ft and a BET surface area of 50 to 250 $m^2g$.

2. A low structure amorphous silicon dioxide characterized by containing 10 wt % moisture, 5% pH of 7.0, oil absorption of less than 125 cc/100 gm, a refractive index of 1.45; an APS of 11 microns, a density of 17 lbs/cu.ft., a percent abrasive fluoride compatibility of at least 90 percent, and a BET surface area of 50 to 250 $m^2/g$.

* * * * *